(12) United States Patent
Sakaguchi

(10) Patent No.: US 10,932,752 B2
(45) Date of Patent: Mar. 2, 2021

(54) CATHETER

(71) Applicant: TERUMO KABUSHIKI KAISHA, Tokyo (JP)

(72) Inventor: Yuuki Sakaguchi, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 352 days.

(21) Appl. No.: 15/921,764

(22) Filed: Mar. 15, 2018

(65) Prior Publication Data

US 2018/0199912 A1    Jul. 19, 2018

Related U.S. Application Data

(63) Continuation-in-part of application No. PCT/JP2016/072067, filed on Jul. 27, 2016.

(30) Foreign Application Priority Data

Sep. 18, 2015   (JP) .............................. JP2015-185953

(51) Int. Cl.
*A61B 8/14*    (2006.01)
*A61B 8/12*    (2006.01)
(Continued)

(52) U.S. Cl.
CPC .............. *A61B 8/12* (2013.01); *A61B 5/0035* (2013.01); *A61B 5/0084* (2013.01);
(Continued)

(58) Field of Classification Search
None
See application file for complete search history.

(56) References Cited

U.S. PATENT DOCUMENTS 5,827,313 A    10/1998  Ream
6,004,271 A    12/1999  Moore
(Continued)

FOREIGN PATENT DOCUMENTS

EP    0 958 795 A2    11/1999
JP    3130047 B2     1/2001
(Continued)

OTHER PUBLICATIONS

English Translation of the Written Opinion (PCT/ISA/237) dated Oct. 25, 2016, by the Japan Patent Office as the ISA for the International Application No. PCT/JP2016/072067.
(Continued)

*Primary Examiner* — Joel F Brutus
(74) *Attorney, Agent, or Firm* — Buchanan Ingersoll & Rooney PC

(57) ABSTRACT

A catheter includes a first structure having an elongated catheter body with at least one lumen and a first connection portion. The catheter includes a second structure that has a second connection portion which is connectable to the distal side of the first connection portion and a third structure that has an inner tube in which an elongated imaging core having an image capturing unit for capturing an image is positionable and a third connection portion which is connectable to the proximal side of the first connection portion. The catheter includes a first prevention portion to prevent the first connection portion from connecting to the third connection portion when the first and second connection portions are connected and a second prevention portion to prevent the first connection portion from connecting to the second connection portion when the first and third connection portions are connected.

19 Claims, 5 Drawing Sheets

(51) Int. Cl.
- *A61M 39/10* (2006.01)
- *A61B 5/02* (2006.01)
- *A61B 5/00* (2006.01)
- *A61B 8/00* (2006.01)

(52) U.S. Cl.
CPC ......... *A61B 5/02007* (2013.01); *A61M 39/10* (2013.01); *A61B 5/0066* (2013.01); *A61B 5/6852* (2013.01); *A61B 8/445* (2013.01); *A61B 8/4461* (2013.01)

(56) References Cited

U.S. PATENT DOCUMENTS

| | | | |
|---|---|---|---|
| 2014/0371598 A1* | 12/2014 | Okubo | A61B 8/0891 600/467 |
| 2016/0143616 A1 | 5/2016 | Okubo et al. | |

FOREIGN PATENT DOCUMENTS

| | | |
|---|---|---|
| JP | 2001-513659 A | 9/2001 |
| JP | 2002-513607 A | 5/2002 |
| JP | 2015-066036 A | 4/2015 |
| WO | 2014/188969 A1 | 11/2014 |

OTHER PUBLICATIONS

International Search Report (PCT/ISA/210) dated Oct. 25, 2016, by the Japanese Patent Office as the International Searching Authority for International Application No. PCT/JP2016/072067.

Written Opinion (PCT/ISA/237) dated Oct. 25, 2016, by the Japanese Patent Office as the International Searching Authority for International Application No. PCT/JP2016/072067.

Office Action (Notice of Reasons for Refusal) dated Mar. 10, 2020, by the Japanese Patent Office in corresponding Japanese Patent Application No. 2017-539748 and an English Translation of the Office Action. (6 pages).

* cited by examiner

CATHETER

CROSS-REFERENCES TO RELATED APPLICATIONS

This application is a continuation of International Application No. PCT/JP2016/072067 filed on Jul. 27, 2016, and claims priority to Japanese Patent Application No. 2015-185953 filed on Sep. 18, 2015, the entire content of both of which is incorporated herein by reference.

TECHNICAL FIELD

The present invention generally relates to a catheter.

BACKGROUND DISCUSSION

A catheter is known which can be inserted into a body lumen such as a blood vessel and used to diagnose an inside of the body lumen by using an ultrasound wave or light. For example, Japanese Patent Application Publication No. 2001-513659 discloses a catheter which can be used in this manner.

According to the catheter disclosed in Japanese Patent Application Publication No. 2001-513659, a drive cable is inserted into a distal portion of the catheter. The drive cable transmits and receives the ultrasound wave so as to acquire an ultrasound image. The drive cable is rotated around its axis when the drive cable is inserted into the catheter and the catheter remains fixed, and the drive cable is moved in a proximal direction. In this manner, the ultrasound image can be acquired from the inside of the body lumen.

On the other hand, for example, the in some cases the drive cable is not moved in the proximal direction while the catheter remains fixed depending on a type of lesion in the body lumen. Alternatively, the drive cable may be moved in the proximal direction together with the catheter. However, this operation cannot be performed in a case of using the catheter disclosed in Japanese Patent Application Publication No. 2001-513659.

In other words, a user cannot switch between an operation for moving only the drive cable while the catheter is fixed and an operation for moving both the catheter and the drive cable when using a catheter such as the one disclosed in Japanese Patent Application Publication No. 2001-513659. Consequently, in practice, this type of catheter cannot necessarily meet clinical demands.

SUMMARY

The catheter disclosed in this application may allow, for example, a user to safely and reliably switch operations, such as an operation for maintaining a positional relationship between a catheter body and an imaging core and an operation for changing the positional relationship, depending on the clinical case.

The catheter disclosed here may involve the following aspects (1) to (8).

(1) A catheter including a first structure that has an elongated catheter body having at least one lumen, and a first connection portion disposed on a proximal side of the catheter body, a second structure that has a second connection portion which is connectable to the first connection portion on a distal side of the first connection portion, a third structure that has an inner tube which an elongated imaging core having an image capturing unit for capturing an image and extending to the inside of the catheter body is inserted, and a third connection portion which is disposed on a proximal side of the inner tube and which is connectable to the first connection portion on a proximal side of the first connection portion, a first prevention portion that prevents connection between the first connection portion and the third connection portion, in a first connection state where the first connection portion and the second connection portion are connected to each other, and a second prevention portion that prevents connection between the first connection portion and the second connection portion, in a second connection state where the first connection portion and the third connection portion are connected to each other.

(2) In the catheter described in (1) above, in the first connection state, the imaging core is movable forward to and rearward from the catheter body along a longitudinal direction of the imaging core. In the second connection state, the catheter body and the imaging core are collectively movable along the longitudinal direction.

(3) In the catheter described in (1) or (2) above, the first prevention portion is disposed in a distal side relative to the third connection portion included in the third structure. The second prevention portion is disposed in a proximal side relative to the second connection portion included in the second structure.

(4) In the catheter described in any one (1) to (3) above, a length of the first prevention portion which extends along the longitudinal direction of the catheter is longer than a length of a protruding portion in which the first connection portion brought into the first connection state protrudes in a proximal direction toward the second structure. A length of the second prevention portion which extends along the longitudinal direction of the catheter is longer than a length of a protruding portion in which the first connection portion brought into the second connection state protrudes in a distal direction toward the third structure.

(5) In the catheter described in any one (1) to (4) above, the first connection portion has a male screw, and the third connection portion has a female screw into which the male screw is screwed. The first prevention portion is configured to include a large diameter portion having an inner diameter which is larger than an outer diameter of the male screw.

(6) In the catheter described in any one (1) to (5) above, the first connection portion has a male screw, and the second connection portion has a female screw into which the male screw is screwed. The second prevention portion is configured to include a large diameter portion having an inner diameter which is larger than an outer diameter of the male screw.

(7) In the catheter described in any one (1) to (6) above, the inner tube interlocks with the first structure, regardless of the first connection state and the second connection state.

(8) In the catheter described in any one (1) to (7) above, the lumen includes an imaging core lumen into which the imaging core is inserted, and a guide wire lumen into which a guide wire is inserted.

Another aspect of the disclosure involves a catheter that includes a first structure having an elongated catheter body with at least one lumen and a first connection portion. The catheter includes a second structure that has a second connection portion which is connectable to the distal side of the first connection portion and a third structure that has an inner tube in which an elongated imaging core having an image capturing unit for capturing an image is positionable and a third connection portion which is connectable to the proximal side of the first connection portion. The catheter includes a first prevention portion to prevent the first connection portion from connecting to the third connection portion when the first and second connection portions are connected and a second prevention portion to prevent the first connection portion from connecting to the second connection portion when the first and third connection portions are connected.

This application also disclose a catheter that includes an elongated catheter body comprising at least one lumen, the catheter body extending in an axial direction from a proximal end to a distal end; a first connection portion comprising a distal protrusion, a middle portion, and a proximal protrusion, the distal protrusion extending distally from the middle portion in the axial direction and the proximal protrusion extending proximally from the middle portion in the axial direction, the distal protrusion of the first connection portion being integrally formed in one piece with the proximal end of the catheter body; a second connection portion positioned distal to the first connection portion, the second connection portion being connectable to the distal protrusion of the first connection portion so that the first connection portion and the catheter body are fixed to the second connection portion; a third connection portion positioned proximal to the first connection portion, the third connection portion being connectable to the proximal protrusion of the first connection portion so that the first connection portion and the catheter body move with the third connection portion, the third connection portion comprising a lumen that communicates with the lumen of the catheter body, an elongated image core being positionable in the lumen of the third connection portion and in the lumen of the catheter body; and the third connection portion being movable relative to the second connection portion, the first connection portion and the catheter body moving with the third connection portion relative to the second connection portion when the first connection portion is connected to the third connection portion, and the first connection portion and the catheter main body being fixed to the second connection portion during movement of the third connection portion relative to the second connection portion when the first connection portion is connected to the second connection portion.

Yet another aspect involves an imaging method for imaging a body lumen inside of a living body. The method includes: grasping an outer surface of a distal connection body of a catheter, the catheter comprising an elongated main body extending through the distal connection body in an axial direction and a proximal connection body distal to the distal connection body, the elongated main body comprising a lumen and an imaging core in the lumen; connecting the proximal connection body to an axial moving device; inserting a portion of the elongated main body of the catheter and the imaging core into the living body; connecting the elongated main body to the distal connection body and imaging the body lumen while proximally moving the imaging core in the axial direction relative to the elongated main body by moving the proximal connection body proximally with the axial moving device; releasing the connection of the elongated main body to the distal connection body; and after the releasing, connecting the elongated main body to the proximal connection body and imaging the body lumen while proximally moving both the imaging core and the elongated main body in the axial direction by moving the proximal connection body proximally with the axial moving device.

The disclosed connection combination among a first structure, a second structure, and a third structure helps enable a user to safely and reliably switch operations such as an operation for maintaining a positional relationship between a catheter body and an imaging core and an operation for changing the positional relationship. It is thus possible to reliably prevent inadvertent connection between the first structure and the third structure, or inadvertent connection between the first structure and the second structure during these operations. Therefore, the catheter is excellent in safety and operability (usability).

DETAILED DESCRIPTION

Figure 1:
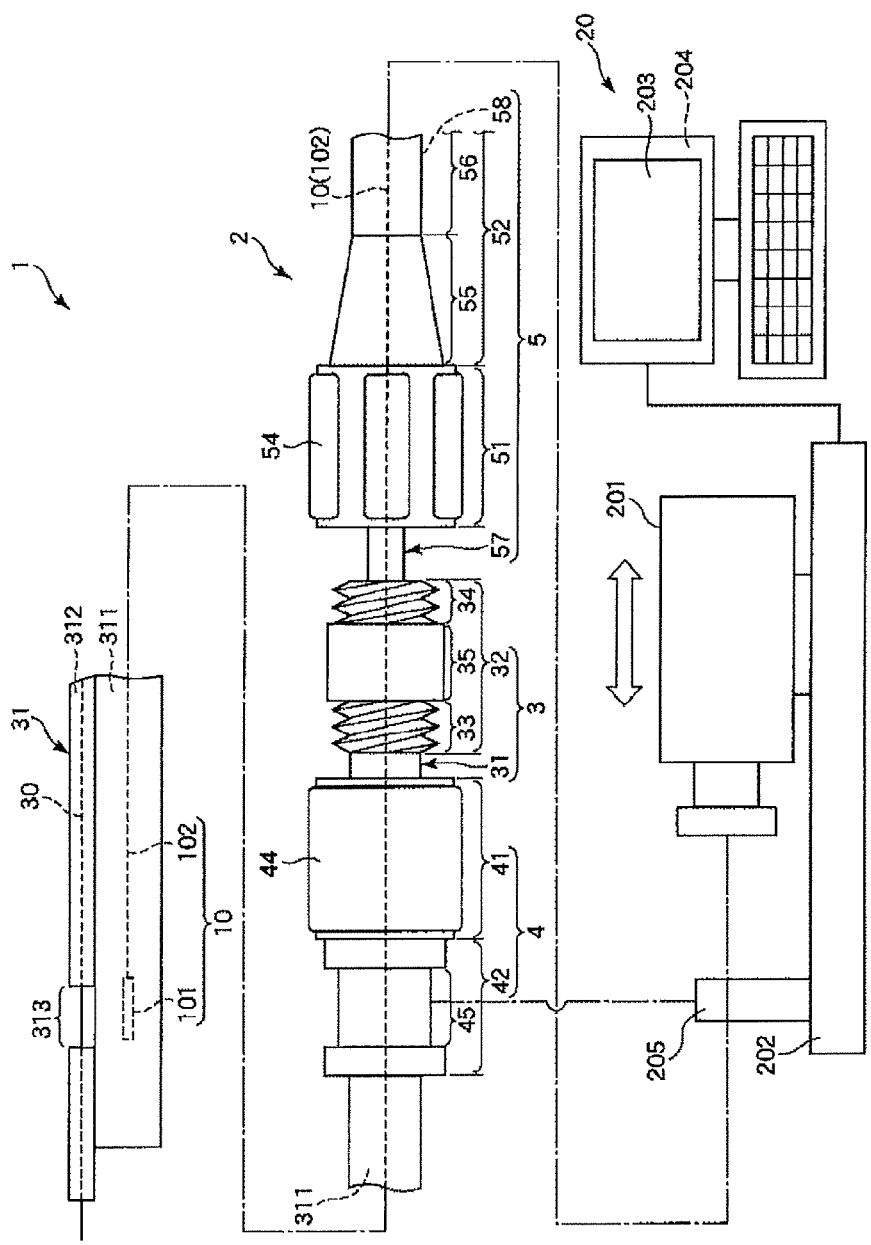
FIG. 1 is an exploded side view illustrating a use state of a first embodiment of a catheter.

Set forth below with reference to the accompanying drawings is a detailed description of embodiments of a catheter representing examples of the inventive catheter disclosed here. In some cases, a dimension ratio in the drawings may be exaggerated and different from a ratio used in practice in order to facilitate the description.

First Embodiment

Figures 2A, 2B:
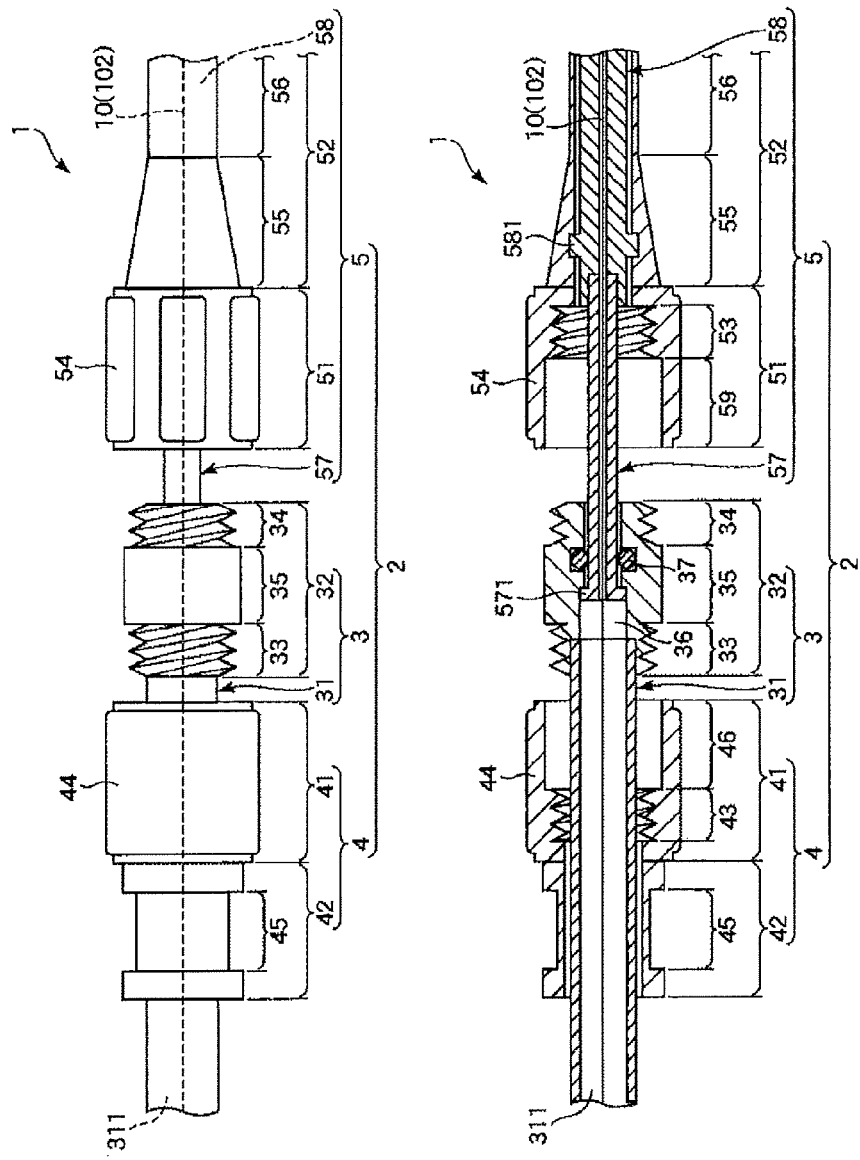
FIG. 2A is an exploded side view and FIG. 2B is an exploded vertical cross-sectional view in the vicinity of a proximal portion of the catheter illustrated in FIG. 1.
Figure 3:
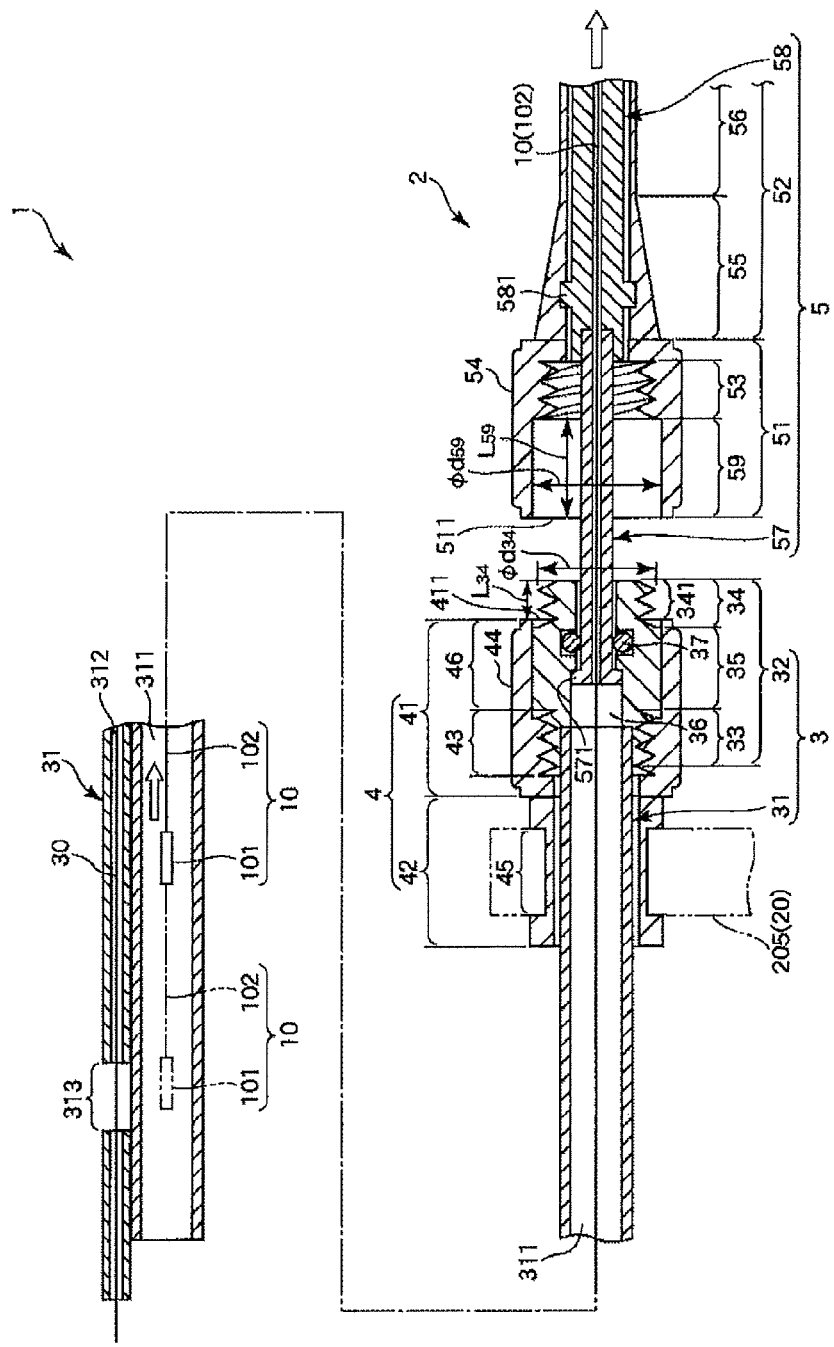
FIG. 3 is a vertical cross-sectional view illustrating a first connection state of the catheter illustrated in FIG. 1.
Figure 4:
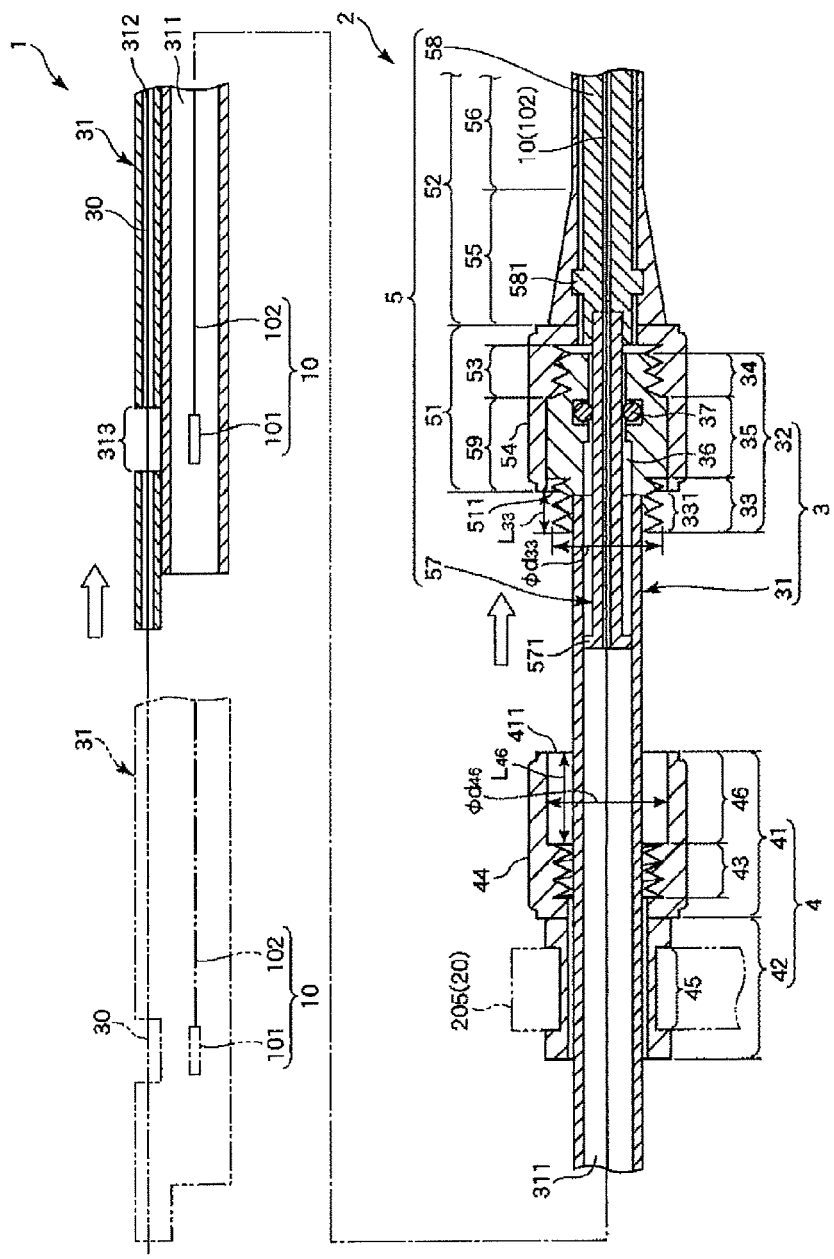
FIG. 4 is a vertical cross-sectional view illustrating a second connection state of the catheter illustrated in FIG. 1.

FIG. 1 is an exploded side view illustrating a use state of a catheter (first embodiment) according to the present invention. FIG. 2A is an exploded side view, and FIG. 2B is an exploded vertical cross-sectional view in the vicinity of a proximal portion of the catheter illustrated in FIG. 1. FIG. 3 is a vertical cross-sectional view illustrating a first connection state of the catheter illustrated in FIG. 1. FIG. 4 is a vertical cross-sectional view illustrating a second connection state of the catheter illustrated in FIG. 1. Hereinafter, for convenience of description, a right side in FIGS. 1-5 (i.e., the side operated by an operator) will be referred to as a "proximal", "proximal end" or "proximal side", and a left side (i.e., a side inserted into a living body) will be referred to as a "distal", "distal end" or "distal side".

A catheter assembly 1 illustrated in FIG. 1 includes a catheter 2 and an imaging core 10 inserted into the catheter 2. In an assembled state where the catheter 2 and the imaging core 10 are assembled, this catheter assembly 1 is used by being inserted into a body lumen (hereinafter, a "blood vessel" is described as a representative example of a body lumen) so as to acquire a vascular wall image serving as an internal image of the body lumen.

For example, the catheter 2 may be used for an intravascular ultrasound (IVUS) in which image diagnosis is performed using an ultrasound wave, an optical coherence tomography (OCT) apparatus in which the image diagnosis is performed using an optical signal, or an optical frequency domain imaging (OFDI) apparatus which is an improved version of the OCT apparatus and utilizes wavelength sweep. For example, when the catheter 2 serves as the catheter for intravascular ultrasound (IVUS), biological tissue is irradiated with an ultrasound wave emitted from a distal portion of the imaging core 10 (described in more detail later). A cross-sectional image of the blood vessel can thus be extracted based on a reflected wave of the ultrasound wave emitted from the distal portion of the imaging core 10. On the other hand, when the catheter 2 serves as the catheter for optical interference tomographic image diagnosis (OCT/ OFDI), the biological tissue is irradiated with a near-infrared ray emitted from the distal portion of the imaging core 10. Interference light is generated by causing reflected light from the biological tissue to interfere with reference light. The cross-sectional image of the blood vessel can thereafter be extracted based on the interference light.

The catheter assembly 1 is used by being connected to an external unit 20. The external unit 20 has a scanner device 201 internally equipped with an external drive source such as a motor, an axial moving device 202 that grips the scanner device 201 and moves the scanner device 201 in a horizontal direction (i.e., an axial direction) by using a motor, a control unit 203 that has a function to control each operation of the scanner device 201 and the axial moving device 202, and a display unit 204 that displays a vascular wall image obtained by the catheter assembly 1 (i.e., obtained by the imaging core 10 of the catheter assembly 1).

The external unit 20 will be described prior to the description of the catheter assembly 1.

A proximal portion of the catheter assembly 1 is freely detachably connected (i.e., the proximal portion of the catheter assembly 1 is attachable to and removable from the scanner device 201) to the scanner device 201. The scanner device 201 can rotate the imaging core 10 around the axis of the imaging core 10 when the proximal portion of the catheter assembly 1 is connected to the scanner device 201. In addition, the scanner device 201 can cause the axial moving device 202 to move the imaging core 10 alone (i.e., without moving the catheter 2) or together with a portion of the catheter 2 in the axial direction. In this manner, an image capturing unit 101 of the imaging core 10 can scan the inside of the blood vessel. In addition, the external unit 20 forms the vascular wall image based on information obtained from the imaging core 10 transmitted via the scanner device 201. The cross-sectional image inside the blood vessel may thus be obtained at any desired position of the blood vessel over the entire periphery in a circumferential direction of the blood vessel.

An engagement portion 205 with which a portion of the catheter 2 engages is disposed on a distal side of the axial moving device 202 relative to the scanner device 201 (i.e., the engagement portion 205 is distal to the distal end of the scanner device 201).

For example, the control unit 203 is a personal computer internally equipped with a central processing unit (CPU). In addition, the display unit 204 is, for example, a liquid crystal display.

Next, the catheter assembly 1 will be described.

As described above, the catheter assembly 1 includes the catheter 2 and the imaging core 10.

The imaging core 10 has a shaft portion 102 (i.e., a shaft) which is a flexible and elongated body, and the image capturing unit 101 fixed to the distal portion of the shaft portion 102.

The shaft portion 102 has such a sufficient length to help enable the image capturing unit 101 to extend to the inside of a catheter body 31 (described below) of the catheter 2 when in an assembled state (i.e., when the imaging core 10 is inserted into the catheter 2).

The image capturing unit 101 may include, for example, an ultrasound transducer to transmit and receive the ultrasound wave and to image the ultrasound image and capture it. In this manner, ultrasonography can be performed by the image capturing unit 101.

As illustrated in FIGS. 1-4, the catheter 2 includes a first structure 3 (i.e., a distal connection body), a second structure 4 (i.e., a middle connection body), and a third structure 5 (i.e., a proximal connection body). In the catheter assembly 1, each proximal side of the third structure 5 and the imaging core 10 interlocks with the scanner device 201. In other words, the scanner device 201 is detachably connects simultaneously to both the third structure 5 and the imaging core 10.

As illustrated in FIGS. 2A and 2B (also illustrated in FIGS. 1, 3, and 4), the first structure 3 includes a catheter body 31 and a first connecting operation member 32. The catheter body 31 is integrally formed in one piece with the first connecting operation member 32 as shown in FIG. 1.

The catheter body 31 is, for example, a flexible and elongated tube that has an imaging core lumen 311 and a guide wire lumen 312 (e.g., as shown in FIG. 1).

The imaging core lumen 311 serves as a lumen into which the imaging core 10 can be inserted (i.e., the imaging core lumen 311 is configured to receive the imaging core 10). The imaging core lumen 311 is formed along the longitudinal direction (i.e., axial direction) of the catheter body 31. When the imaging core 10 is inserted into the imaging core lumen 311, the ultrasonography can be performed.

The guide wire lumen 312 serves as a lumen into which a guide wire 30 can be inserted (i.e., the guide wire lumen 312 is configured to receive a guide wire). The guide wire lumen 312 is formed adjacent to the imaging core lumen 311 and extends parallel to the imaging core lumen 311 (i.e., in the axial direction). When the guide wire 30 is inserted into the guide wire lumen 312, the catheter body 31 can be caused to easily and reliably reach a target site inside the blood vessel. The guide wire lumen 312 is unevenly located on the distal side of the catheter body 31 (i.e., the guide wire lumen 312 is only provided on the distal side of the catheter body 31), and is shorter than the imaging core lumen 311.

In addition, the guide wire lumen 312 has a vacant portion 313 formed by forming an intermediately vacant portion (i.e., a gap) in a longitudinal direction of the catheter body 31. This vacant portion 313 serves as a portion which the image capturing unit 101 faces during the ultrasonography.

The catheter body 31 material is a material through which the ultrasound wave is permeable. For example, it is preferable to use a fluororesin such as polytetrafluoroethylene (PTFE). In addition, the catheter body 31 may be flexible over the total length. However, the configuration is not limited to the catheter body 31 being flexible over the entirety of the length of the catheter body 31. For example, the distal side of the catheter body 31 may be flexible, and the proximal side of the catheter body 31 may be harder (i.e., more rigid) than the distal side.

The total length of the catheter body 31 is not particularly limited and may be appropriately determined depending on a use site of the catheter 2, a clinical case or the like. However, it is normally preferable that the total length of the catheter body 31 is approximately 1,400 to 1,700 mm.

As illustrated in FIGS. 2A and 2B, the first connecting operation member 32 is disposed in the proximal portion (proximal side) of the catheter body 31. The first connecting operation member 32 is a member for performing a connecting operation when the first structure 3 and the second structure 4 are connected to each other (e.g., as shown in FIG. 3).

The first connecting operation member 32 has a cylindrical shape and includes a distal male screw 33 and a proximal male screw 34 which serve as a first connection portion in the outer peripheral portion. The distal male screw 33 is formed on the distal side of the outer peripheral portion of the first connecting operation member 32, and the proximal male screw 34 is formed on the proximal side of the outer peripheral portion of the first connecting operation member 32. Preferably, the distal male screw 33 and the proximal male screw 34 have the same screwing direction and the same screwing pitch. However, the screwing directions may be opposite to each other, and the screwing pitches may be different from each other.

The portion extending between the distal male screw 33 and the proximal male screw 34 (i.e., in the axial direction) functions as a grip portion 35 gripped when the connecting operation between the first structure 3 and the second structure 4 is performed.

The proximal portion of the catheter body 31 is inserted into the first connecting operation member 32, that is, the lumen portion 36 of the first connecting operation member 32, and is fixed in a liquid-tight manner. This fixing method is not particularly limited. Examples of this fixing method include using adhesion (bonding with an adhesive or a solvent), and using fusion bonding (heat-welding, high frequency welding, ultrasound welding or the like).

The first connecting operation member 32 material may preferably be a material which is harder than the catheter body 31 material. For example, the material of the first connecting operation member 32 may be polyolefin.

As illustrated in FIGS. 2A and 2B, the second structure 4 includes a second connecting operation member 41 and a rotation support member 42. The rotation support member 42 rotatably supports the second connecting operation member 41.

The second connecting operation member 41 has a cylindrical shape and includes a female screw 43 serving as a second connection portion in the inner peripheral portion of the second connecting operation member 41. The female screw 43 is formed so as to be unevenly located on the distal side in the inner peripheral portion of the second connecting operation member 41 (i.e., the female screw 43 is only provided in the distal portion of the second connecting operation member 41). Then, the female screw 43 can be screwed to the distal male screw 33 of the first connecting operation member 32 (i.e., the distal male screw 33 is threadably engageable with the female screw 43). As illustrated in FIG. 3, this screwing (of the distal male screw 33 into the female screw 43) allows a first connection state where the first structure 3 (first connection portion) and the second structure 4 (second connection portion) are connected to each other, so that the first structure 3 and the second structure 4 move together, e.g., in the axial direction.

In addition, the outer peripheral portion of the second connecting operation member 41 functions as a grip portion 44 gripped when the female screw 43 and the distal male screw 33 are screwed together or unscrewed from one another.

The rotation support member 42 is disposed on the distal side of the second connecting operation member 41 (i.e., the rotation support member 42 is distal to the distal end of the second connecting operation member 41). Similarly to the second connecting operation member 41, the rotation support member 42 has a cylindrical shape. The rotation support member 42 supports the second connecting operation member 41 so that the second connecting operation member 41 is rotatable around the central axis. This support structure is not particularly limited. For example, the support structure can be configured to include a ring-shaped convex portion formed along the circumferential direction of one of the second connecting operation member 41 or the rotation support member 42 and a corresponding ring-shaped concave portion which is formed along the circumferential direction of the other member and into which the convex portion is fitted. The second connecting operation member 41 may thus be rotationally operated (i.e., rotated) with respect to the rotation support member 42. In this manner, the female screw 43 and the distal male screw 33 can be screwed together.

In addition, the catheter body 31 is inserted into the rotation support member 42 (i.e., the catheter body 31 extends through the interior of the rotation support member 42).

A decreased diameter portion 45 having a decreased diameter is formed in the outer peripheral portion of the rotation support member 42. The decreased diameter portion 45 can engage with the engagement portion 205 of the external unit 20. In this manner, regardless of the rotation or the movement of the imaging core 10, as illustrated in FIGS. 3 and 4, a position of the second structure 4 is restricted.

The second connecting operation member 41 and the rotation support member 42 can be the same material as any of those that can be used for the first connecting operation member 32.

As illustrated in FIGS. 2A and 2B, the third structure 5 includes a third connecting operation member 51, a rotation support member 52 which rotatably supports the third connecting operation member 51, an inner tube 57 which is inserted into the third connecting operation member 51 (i.e., within an interior or within a lumen of the third connecting operation member 51), and an interlock tube 58 which interlocks with the inner tube 57.

The third connecting operation member 51 has a cylindrical shape and includes a female screw 53 serving as a third connection portion in the inner peripheral portion. The female screw 53 is unevenly located on the proximal side in the inner peripheral portion of the third connecting operation member 51 (i.e., the female screw 53 is only provided in the proximal portion of the third connecting operation member 51) and is formed so as to face the proximal portion (proximal side) of the inner tube 57 (i.e., the inner surface of the female screw 53 directly faces the outer surface of the inner tube 57 along a proximal portion of the inner tube 57 as shown in FIG. 3). The female screw 53 can be screwed to the proximal male screw 34 of the first connecting operation member 32. As illustrated in FIG. 4, this screwing allows a second connection state where the first structure 3 (first connection portion) and the third structure 5 (third connection portion) are connected to each other, so that the first structure 3 and the third structure 5 move together, e.g., in the axial direction.

In addition, the outer peripheral portion of the third connecting operation member 51 functions as a grip portion 54 gripped when the female screw 53 and the proximal male screw 34 are screwed together or unscrewed from one another.

The rotation support member 52 is disposed on the proximal side of the third connecting operation member 51 (i.e., the rotation support member 52 is proximal to the proximal end of the third connecting operation member 51). Similarly to the third connecting operation member 51, the rotation support member 52 has a cylindrical shape and supports the third connecting operation member 51 that the third connecting operation member 51 is rotatable around the central axis. This support structure is not particularly limited. For example, the support structure can be configured to include a ring-shaped convex portion formed along the circumferential direction of one of the third connecting operation member 51 or the rotation support member 52, and a corresponding ring-shaped concave portion formed along the circumferential direction of the other member and into which the convex portion is fitted. Then, the female screw 53 and the proximal male screw 34 can be screwed together by rotating the third connecting operation member 51 with respect to the rotation support member 52.

The outer peripheral portion of the rotation support member 52 has a gradually decreased outer diameter portion (tapered portion) 55 whose outer diameter gradually decreases (tapers) in the proximal direction. The rotation support member 52 also includes a constant outer diameter portion 56 which is proximal to the gradually decreased outer diameter portion 55 and whose outer diameter is constant.

The imaging core 10 is inserted into the inner tube 57 (i.e., the inner tube 57 is configured to receive the imaging core 10 in an interior of the inner tube 57). The inner tube 57 is disposed concentrically inside the third connecting operation member 51. The inner tube 57 is inserted into the first connecting operation member 32 from the proximal side. The distal portion of the inner tube 57 includes a large-diameter portion 571 whose outer diameter is increased. The large-diameter portion 571 engages with the inner peripheral portion of the first connecting operation member 32 to function as a stopper for preventing the inner tube 57 from being pulled out from the first connecting operation member 32 (e.g., as shown in FIGS. 2 and 3). The inner tube 57 thus remains interlocked with the first connecting operation member 32 regardless of the first connection state and/or second connection state. Accordingly, the inner tube 57 can communicate with the imaging core lumen 311 of the catheter body 31.

The inner peripheral portion (lumen portion 36) of the first connecting operation member 32 includes a ring-shaped sealing material 37 attached to the outer peripheral portion of the inner tube 57. When priming is performed on the imaging core lumen 311, the ring-shaped sealing material 37 helps prevent a priming solution from leaking out between the inner peripheral portion of the first connecting operation member 32 and the outer peripheral portion of the inner tube 57.

The interlock tube 58 interlocks and communicates with the proximal portion of the inner tube 57, and the imaging core 10 is inserted into the interlock tube 58 (i.e., within a lumen of the interlock tube 58 as shown in FIG. 3), similarly to the insertion of the imaging core 10 within the inner tube 57. The interlock tube 58 is disposed concentrically inside the rotation support member 52. A large-diameter portion 581 whose outer diameter is increased (relative to the outer diameter of the rest of the interlock tube 58) is formed in the intermediate portion of the interlock tube 58 in the longitudinal direction. The large-diameter portion 581 engages with the inner peripheral portion of the rotation support member 52 to function as a stopper for preventing the interlock tube 58 from being pulled out from the rotation support member 52.

The material(s) used to form the third connecting operation member 51, the rotation support member 52, the inner tube 57, and the interlock tube 58 may be any of the same materials as those which can be used for the first connecting operation member 32.

In a clinical field, a user of the catheter 2 needs to acquire a desired vascular cross-sectional image by appropriately changing an operation for causing the catheter 2 to acquire the image in accordance with a lesion condition inside the blood vessel. For example, in order to perform the image diagnosis on a meandering vascular site or at the inside of a blood vessel having progressed stenosis or a calcification site, it is preferable to acquire the image while the position of the catheter body 31 is fixed by moving the imaging core 10 forward to (distally) and rearward (proximally) relative to the catheter body 31. This operation of the catheter 2 enables the image to be very accurately acquired, even inside a blood vessel that possesses a complicated structure. On the other hand, depending on a clinical case, it may be preferable to acquire the image by causing the catheter body 31 and the imaging core 10 to integrally move forward (distally) and rearward (proximally) together with one another.

As illustrated in FIG. 3, the rotation support member 42 of the second structure 4 of the catheter 2 engages with the engagement portion 205 of the external unit 20. In this manner, the second structure 4 is brought into a state where the position of the second structure 4 is restricted (i.e., the second structure 4 is fixed or held in a fixed state).

The catheter 2 is in the first connection state when the first structure 3 and the second structure 4 are connected to each other. In the first connection state, the first structure 3 is connected to the second structure 4 in the state where the position of the second structure 4 is restricted. Accordingly, the first structure 3 is also in the state where its position is restricted.

Then, the axial moving device 202 is operated in a state where the position of the first structure 3 and the second structure 4 is restricted with respect to the engagement portion 205 of the external unit 20. In this manner, the imaging core 10 can be moved in the proximal direction along the longitudinal direction (i.e., moved proximally in the axial direction) of the catheter body 31. It is thus possible to acquire an image of the intravascular wall by performing an operation for relatively moving the imaging core 10 in the proximal direction (hereinafter, referred to as a "first operation") with respect to the catheter body 31 whose position is fixed to the engagement portion 205 of the external unit 20 (i.e., the imaging core 10 moves proximally relative to the catheter body 31 while the position of the catheter body 31 is fixed).

When the first operation is performed, it is necessary to prevent a connection between the first structure 3 and the third structure 5. The reason is as follows. If the first structure 3 and the third structure 5 are connected to each other, the first structure 3 may be, for example, pulled in the proximal direction together with the imaging core 10 via the third structure 5. As a result, a force may be applied to move the catheter body 31 (whose position is fixed to the engagement portion 205 of the external unit 20) in the proximal direction, and thus, due to an inadvertent operation, a state where the position of the second structure 4 is restricted by the engagement portion 205 of the external unit 20 is released. Consequently, the engagement portion 205 of the external unit 20 may be damaged. Furthermore, in a case where the first operation cannot be properly performed because of the releasing of the second structure 4, there is a possibility that the catheter 2 may be damaged and that it may be difficult to acquire the desired image.

Therefore, the third structure 5 is provided with a first prevention portion 59 which prevents the connection between the first structure 3 and the third structure 5 in the first connection state.

The first prevention portion 59 is configured to include a large diameter portion whose inner diameter is $\phi d_{59}$ on the distal side relative to the female screw 53 of the third connecting operation member 51 (i.e., the first prevention portion 59 is distal to the distal end of the female screw 53). This inner diameter $\phi d_{59}$ is larger than the outer diameter $\phi d_{34}$ of the proximal male screw 34 of the first structure 3.

In addition, a length $L_{59}$ of the first prevention portion 59 along the longitudinal direction (rightward-leftward direction in FIG. 3) of the catheter 2 is longer than a length $L_{34}$ of a protruding portion 341 which is the length that the proximal male screw 34 protrudes from a proximal end surface 411 of the second structure 4 in the proximal direction in the first connection state.

Since the first prevention portion 59 is configured in this way, even if the proximal male screw 34 of the first structure 3 is inserted into the third connecting operation member 51 of the third structure 5 and is attempted to be screwed into the female screw 53, the proximal male screw 34 does not reach the female screw 53. The third connecting operation member 51 thus runs idle (i.e., rotates without forming a connection). In this manner, it is possible to reliably prevent the connection between the first structure 3 and the third structure 5 in the first connection state (i.e., when the first structure 3 is connected to the second structure 4). Accordingly, it is possible to reliably prevent the above-described first structure 3 from being pulled in the proximal direction together with the imaging core 10 in the first operation. Therefore, the first operation can be reliably performed according to this configuration.

As illustrated in FIG. 4, similarly to FIG. 3, the rotation support member 42 of the second structure 4 of the catheter 2 engages with the engagement portion 205 of the external unit 20. In this manner, the second structure 4 is in a state where the position of the second structure 4 is restricted.

The catheter 2 is in the second connection state when the first structure 3 and the third structure 5 are connected to each other. In the second connection state, the first structure 3 is in a state of being movable along the longitudinal direction of the catheter 2 together with the third structure 5 (i.e., the first structure 3 and the third structure 5 move axially together with one another).

The axial moving device 202 is then operated to collectively move the catheter body 31 and the imaging core 10 in the proximal direction along the longitudinal direction. In this manner, the catheter body 31 and the imaging core 10 are collectively moved and operated while maintaining a state where the image capturing unit 101 faces the vacant portion 313. Accordingly, it is possible to acquire an image of the intravascular wall of the body lumen.

When this operation (hereinafter, referred to as "the second operation") is performed, it is necessary to prevent the connection between the first structure 3 and the second structure 4. The reason is as follows. If the first structure 3 and the second structure 4 are connected to each other, it is extremely difficult to move in the proximal direction with respect to the first structure 3 due to the second structure 4 being in the state where the position is restricted.

Therefore, the second structure 4 is provided with a second prevention portion 46 which prevents the connection between the first structure 3 and the second structure 4 in the second connection state.

The second prevention portion 46 includes a large diameter portion whose inner diameter is $\phi d_{46}$ on the proximal side relative to the female screw 43 of the second connecting operation member 41 (i.e., the second prevention portion 46 is proximal to the proximal end of the female screw 43). This inner diameter $\phi d_{46}$ is larger than an outer diameter $\phi d_{33}$ of the distal male screw 33 of the first structure 3.

In addition, a length $L_{46}$ of the second prevention portion 46 along the longitudinal direction (rightward-leftward direction in FIG. 4) of the catheter 2 is longer than a length $L_{33}$ of a protruding portion 331 which is the length that the distal male screw 33 protrudes from a distal end surface 511 of the third structure 5 in the distal direction in the second connection state.

Since the second prevention portion 46 is configured in this way, even if the distal male screw 33 of the first structure 3 is inserted into the second connecting operation member 3 of the second structure 4 and is attempted to be screwed into the female screw 43, the distal male screw 33 does not reach the female screw 43. The second connecting operation member 41 thus runs idle (i.e., rotates without forming a connection). In this manner, it is possible to reliably prevent the connection between the first structure 3 and the second structure 4 in the second connection state (i.e., when the first structure 3 is connected to the third structure 5). Accordingly, it is possible to reliably prevent a possibility that it may be extremely difficult to pull the first structure 3 in the proximal direction.

As described above, the catheter 2 can easily and reliably switch between the first operation and the second operation by changing between different respective the connections among the first structure 3, the second structure 4, and the third structure 5. This design helps make it possible to reliably prevent the inadvertent connection between the first structure 3 and the third structure 5 in the first operation and reliably prevent the inadvertent connection between the first structure 3 and the second structure 4 in the second operation. Therefore, since the catheter 2 can acquire the image while switching between two operations, the catheter 2 is excellent in safety and operability (usability).

Second Embodiment

Figure 5:
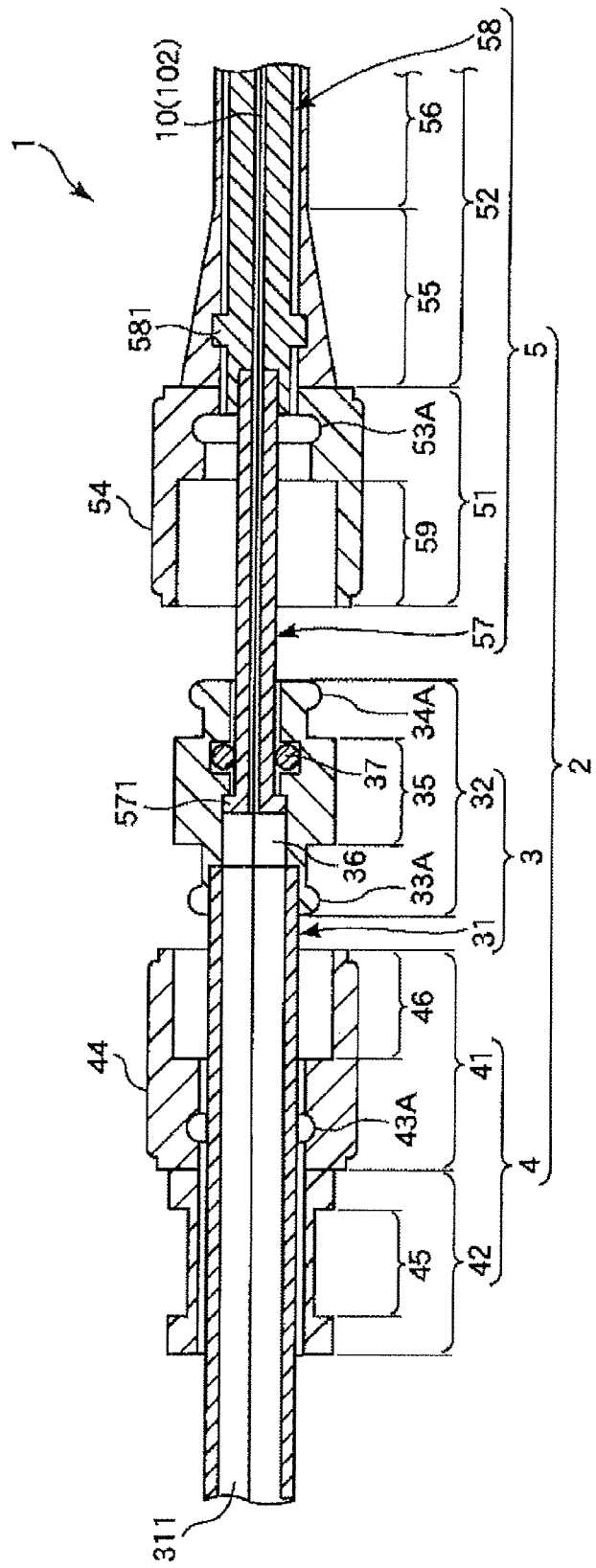
FIG. 5 is an exploded vertical cross-sectional view in the vicinity of a proximal portion of a second embodiment of a catheter.

FIG. 5 is an exploded vertical cross-sectional view in the vicinity of a proximal portion of a catheter (second embodiment) according to the present invention.

The second embodiment of the catheter will be described with reference to FIG. 5. However, points different from those according to the above-described embodiment (the first embodiment) will be mainly described, and description of similar elements will be omitted.

The catheter illustrated in FIG. 5 is similar to the first embodiment of the catheter discussed above, except that the first connection portion, the second connection portion, and the third connection portion have different shapes.

The catheter embodiment illustrated in FIG. 5 has the first connecting operation member 32 which includes a distal convex portion 33A and a proximal convex portion 34A. The distal convex portion 33A and the proximal convex portion 34A serve as the first connection portion in the outer peripheral portion. The distal convex portion 33A and the proximal convex portion 34A protrude to the outer peripheral portion of the first connecting operation member 32 (i.e., protrude radially outwardly from the outer surface of the first connecting operation member 32) and are formed in a ring shape along the circumferential direction of the outer peripheral portion. As shown in FIG. 5 the distal convex portion 33A and proximal convex portion 34A may be necked down from the grip portion 35 (i.e., possess a smaller outer diameter) of the first connecting operation member 32 (this aspect is also shown in FIG. 2 regarding the threaded portions in the first embodiment). It is preferable that each top portion of the distal convex portion 33A and the proximal convex portion 34A is rounded. Furthermore, it is preferable that the distal convex portion 33A and the proximal convex portion 34A are elastic.

The second connecting operation member 41 of the catheter shown in FIG. 5 includes a concave portion 43A serving as the second connection portion in the inner peripheral portion. The concave portion 43A is formed in a ring shape along the inner peripheral portion of the second connecting operation member 41 (i.e., a recess in the inner wall of the second connecting operation member 41). The concave portion 43A can engage with (is configured to engage with) the distal convex portion 33A of the first connecting operation member 32 (i.e., so that the distal convex portion 33A fits within the concave portion 43A). This engagement allows (creates) the first connection state where the first structure 3 and the second structure 4 are connected to each other.

The third connecting operation member 51 includes a concave portion 53A serving as the third connection portion in the inner peripheral portion. The concave portion 53A is formed in a ring shape along the inner peripheral portion of the third connecting operation member 51 (i.e., a recess in the inner wall of the third connecting operation member 51). The concave portion 53A can engage with (is configured to engage with) the proximal convex portion 34A of the first connecting operation member 32 (i.e., so that the proximal convex portion 34A fits within the concave portion 53A). This engagement allows (creates) the second connection state where the first structure 3 and the third structure 5 are connected to each other.

The disclosed catheter has been described with reference to the illustrated embodiments. However, the present invention is not limited thereto, and each element configuring the catheter may be substituted with any desired configuration which can fulfill the same function. In addition, any desired configuration may be added.

The catheter disclosed here may be realized in combination of any two or more configurations (characteristics) from the above-described embodiments. For example, the following configuration can be adopted. The first connection portion and the second connection portion may be connected to each other by means of screwing, and the first connection portion and the third connection portion may be connected to each other by means of concavo-convex engagement. For another example, the first connection portion and the second connection portion may be connected to each other by means of the concavo-convex engagement, and the first connection portion and the third connection portion may be connected to each other by means of screwing.

The catheter body has a plurality of lumens in each of the above-described embodiments. However, the catheter body is not limited in this respect and may, for example, have a single lumen.

The mode in which the second connection portion and the third connection portion are connected to the first connection portion has no problem (i.e., is acceptable) as long as the following configuration is adopted. In a case where one of the second connection portion or the third connection portion is connected to the first connection portion, the other connection portion of the second and third connection portions is in a non-connected state and is prevented from being connected to the first connection portion.

In other words, as the mode in which the second connection portion and the third connection portion are connected to the first connection portion, the screwing is employed in the first embodiment, and the concavo-convex engagement is employed in the second embodiment. However, alternatively, a dial type or a key type connection between the second and/or third connection portions and the first connection portion may be employed. For example, the connection mode may be configured as follows. As the dial type, the first connection portion may have a dial type connection mechanism configured to be rotatable as large as a predetermined angle around the axis of the catheter. The first connection portion may include a grip portion formed to extend to the distal side and the proximal side along the axial direction of the catheter. Based on the rotation direction of the first connection portion, the grip portion fixes only one of the second connection portion or the third connection portion. Alternatively as the key type, if any one of the second connection portion or the third connection portion is connected to the first connection portion, a state where the third connection portion or the second connection portion is connected to the first connection portion is released. That is, the case of the key type has the following structure. The second connection portion and the third connection portion have a relationship of a key hole and a key with the first connection portion.

INDUSTRIAL APPLICABILITY

The disclosed catheter includes a first structure that has an elongated catheter body having at least one lumen, a first connection portion disposed on a proximal side of the catheter body, and a second structure that has a second connection portion. The second connection portion is connectable to the first connection portion on a distal side of the first connection portion. The catheter further includes a third structure that has an inner tube into which an elongated imaging core having an image capturing unit for capturing an image and extending to the inside of the catheter body is inserted, a third connection portion which is disposed on a proximal side of the inner tube and which is connectable to the first connection portion on a proximal side of the first connection portion, a first prevention portion that prevents connection between the first connection portion and the third connection portion in a first connection state where the first connection portion and the second connection portion are connected to each other, and a second prevention portion that prevents connection between the first connection portion and the second connection portion in a second connection state where the first connection portion and the third connection portion are connected to each other. Therefore, for example, depending on a clinical case, a user can safely and reliably switch operations such as an operation for maintaining a positional relationship between a catheter body and an imaging core and an operation for changing the positional relationship. Therefore, the catheter described here has industrial applicability.

The detailed description above describes a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A catheter comprising:
   a first structure comprising an elongated catheter body having at least one lumen and a first connection portion extending proximally from a proximal end of the catheter body, the catheter body extending in an axial direction, the first connection portion comprising a distal side and a proximal side opposite the distal side;

a second structure comprising a second connection portion which is connectable to the distal side of the first connection portion, the second connection portion positioned distal to the first connection portion in the axial direction;

a third structure comprising an inner tube in which an elongated imaging core having an image capturing unit for capturing an image is positionable to extend within the lumen of the catheter body and a third connection portion which is connectable to the proximal side of the first connection portion, the third connection portion positioned proximal to the first connection portion in the axial direction;

a first prevention portion configured to prevent the first connection portion from connecting to the third connection portion when the first connection portion is connected to the second connection portion; and a second prevention portion configured to prevent the first connection portion from connecting to the second connection portion when the first connection portion is connected to the third connection portion.

2. The catheter according to claim 1, wherein when the imaging core is positioned in the inner tube and the first connection portion is connected to the second connection portion, the imaging core is movable distally and proximally relative to the catheter body in the axial direction, and when the imaging core is positioned in the inner tube and the first connection portion is connected to the third connection portion, the catheter body and the imaging core are collectively movable so that the catheter body and the imaging core simultaneously move together in the axial direction.

3. The catheter according to claim 1, wherein the first prevention portion is provided in the third structure, the first prevention portion being distal to the third connection portion of the third structure, and the second prevention portion is provided in the second structure, the second prevention portion being proximal to the second connection portion of the second structure.

4. The catheter according to claim 1, wherein the first connection portion comprises a distal protruding portion and a proximal protruding portion, a length of the first prevention portion in the axial direction is longer than a length of the proximal protruding portion of the first connection portion in the axial direction, and a length of the second prevention portion in the axial direction is longer than a length of the distal protruding portion of the first connection portion in the axial direction.

5. The catheter according to claim 1, wherein the first connection portion comprises a male screw, the third connection portion comprises a female screw threadably engageable with the male screw, and the first prevention portion is a large inner diameter portion of the third connection portion having an inner diameter which is larger than an outer diameter of the male screw.

6. The catheter according to claim 1, the first connection portion comprises a male screw, the second connection portion comprises a female screw threadably engageable with the male screw, and the second prevention portion is a larger inner diameter portion of the second connection portion having an inner diameter which is larger than an outer diameter of the male screw.

7. The catheter according to claim 1, wherein the inner tube interlocks with the first structure when the first connection portion is connected to the second connection portion and when the first connection portion is connected to the third connection portion.

8. The catheter according to claim 1, wherein the at least one lumen of the catheter body comprises an imaging core lumen into which the imaging core is insertable and a guide wire lumen into which a guide wire is insertable.

9. The catheter according to claim 1, wherein the third connection portion possesses an inner surface, the inner tube possesses an outer surface, a distal portion, and a proximal portion, and the inner surface of the third connection portion is fixed to the outer surface of the inner tube along at least a portion of the proximal portion of the inner tube.

10. A catheter comprising:

an elongated catheter body comprising at least one lumen, the catheter body extending in an axial direction from a proximal end of the elongated catheter body to a distal end of the elongated catheter body;

a first connection portion comprising a distal protrusion, a middle portion, and a proximal protrusion, the distal protrusion extending distally from the middle portion in the axial direction and the proximal protrusion extending proximally from the middle portion in the axial direction, the distal protrusion of the first connection portion being integrally formed in one piece with the proximal end of the catheter body;

a second connection portion positioned distal to the first connection portion, the second connection portion being connectable to the distal protrusion of the first connection portion so that the first connection portion and the catheter body are fixed to the second connection portion;

a third connection portion positioned proximal to the first connection portion, the third connection portion being connectable to the proximal protrusion of the first connection portion so that the first connection portion and the catheter body move with the third connection portion, the third connection portion comprising a lumen that communicates with the lumen of the catheter body, an elongated image core being positionable in the lumen of the third connection portion and in the lumen of the catheter body; and the third connection portion being movable relative to the second connection portion, the first connection portion and the catheter body moving with the third connection portion relative to the second connection portion when the first connection portion is connected to the third connection portion, and the first connection portion and the catheter main body being fixed to the second connection portion during movement of the third connection portion relative to the second connection portion when the first connection portion is connected to the second connection portion.

11. The catheter according to claim 10, wherein when the distal protrusion of the first connection portion is connected to the second connection portion, a surface of the third connection portion contacts a surface of the second connection portion before the proximal protrusion of the first connection portions can engage with the third connection portion.

12. The catheter according to claim 10, wherein
when the proximal protrusion of the first connection portion is connected to the third connection portion, a surface of the second connection portion contacts a surface of the third connection portion before the distal protrusion of the first connection portions can engage with the second connection portion.

13. The catheter according to claim 10, wherein
the distal protrusion of the first connection portion comprises outer threads,
the proximal protrusion of the first connection portion comprises outer threads,
the second connection portion comprises inner threads that are threadably engageable with the outer threads of the distal protrusion, and
the third connection portion comprises inner threads that are threadably engageable with the outer threads of the proximal protrusion.

14. The catheter according to claim 10, wherein
one of the distal protrusion of the first connection portion and the second connection portion comprises a convex protrusion extending outward in a radial direction, and
the other of the distal protrusion of the first connection portion and the second connection portion comprises a concave recess extending inward in the radial direction, the convex protrusion being configured to fit within the concave recess.

15. The catheter according to claim 10, wherein
the second connection portion comprises an outer recessed portion which possesses a smaller outer diameter than a remaining portion of the second connection portion, and
the outer recessed portion of the second connection portion is configured to be gripped and held in place when the image core is positioned in the lumen of the catheter body.

16. The catheter according to claim 10, wherein
the second connection portion comprises a larger inner diameter portion and a female screw distal to the larger inner diameter portion, the larger inner diameter portion of the second connection portion possessing a length in the axial direction and an inner diameter greater than an outer dimension of the distal protrusion of the first connection portion;
the third connection portion comprises a larger inner diameter portion and a female screw proximal to the larger inner diameter portion, the larger inner diameter portion of the third connection portion possessing a length in the axial direction and an inner diameter greater than an outer dimension of the proximal protrusion of the first connection portion;
the distal protrusion of the first connection portion possesses a length in the axial direction;
the proximal protrusion of the first connection portion possesses a length in the axial direction;
the length of the distal protrusion of the first connection portion being less than the length of the larger inner diameter portion of the second connection portion; and
the length of the proximal protrusion of the first connection portion being less than the length of the larger inner diameter portion of the third connection portion.

17. An imaging method for imaging a body lumen inside of a living body, the method comprising:
grasping an outer surface of a distal connection body of a catheter, the catheter comprising an elongated main body extending through the distal connection body in an axial direction and a proximal connection body proximal to the distal connection body, the elongated main body comprising a lumen and an imaging core in the lumen;
connecting the proximal connection body to an axial moving device;
inserting a portion of the elongated main body of the catheter and the imaging core into the living body;
connecting a distal side of a connection portion of the elongated main body to the distal connection body and imaging the body lumen while proximally moving the imaging core in the axial direction relative to the elongated main body by moving the proximal connection body proximally with the axial moving device, the connection portion of the elongated main body positioned between the proximal connection body and the distal connection body;
releasing the connection of the elongated main body to the distal connection body; and
after the releasing of the connection of the elongated main body to the distal connection body, connecting a proximal side of the connection portion of the elongated main body, which is opposite the distal side, to the proximal connection body and imaging the body lumen while proximally moving both the imaging core and the elongated main body in the axial direction by moving the proximal connection body proximally with the axial moving device.

18. The method according to claim 17, wherein the catheter comprises a middle connection body positioned between the distal connection body and the proximal connection body in the axial direction, the middle connection body being connected to the distal connection body during the connecting of the elongated main body to the distal connection body and the middle connection body being connected to the proximal connection body during the connecting of the elongated main body to the proximal connection body.

19. The method according to claim 17, further comprising:
preventing the elongated main body from being connected to the distal connection body when the elongated main body is connected to the proximal connection body, and
preventing the elongated main body from being connected to the proximal connection body when the elongated main body is connected to the distal connection body.

* * * * *